(12) United States Patent
Chandran

(10) Patent No.: US 10,842,754 B2
(45) Date of Patent: Nov. 24, 2020

(54) DEOXYRIBONUCLEIC ACID NANOPARTICLES FOR DELIVERING PROTEINS AND PROTEIN-CONTAINING COMPOUNDS AND METHODS OF MANUFACTURING DEOXYRIBONUCLEIC ACID NANOPARTICLES

(71) Applicants: Howard University, Washington, DC (US); Preethi Chandran, Washington, DC (US)

(72) Inventor: Preethi Chandran, Washington, DC (US)

(73) Assignee: HOWARD UNIVERSITY, Washington, DC (US)

( * ) Notice: Subject to any disclaimer, the term of this patent is extended or adjusted under 35 U.S.C. 154(b) by 0 days.

(21) Appl. No.: 16/465,740

(22) PCT Filed: Dec. 1, 2017

(86) PCT No.: PCT/US2017/064245
§ 371 (c)(1),
(2) Date: May 31, 2019

(87) PCT Pub. No.: WO2018/102704
PCT Pub. Date: Jun. 7, 2018

(65) Prior Publication Data
US 2019/0307705 A1 Oct. 10, 2019

Related U.S. Application Data

(60) Provisional application No. 62/429,144, filed on Dec. 2, 2016.

(51) Int. Cl.
| | |
|---|---|
| *A61K 9/51* | (2006.01) |
| *A61K 38/00* | (2006.01) |
| *A61K 47/69* | (2017.01) |
| *A61K 47/59* | (2017.01) |
| *C08G 73/02* | (2006.01) |
| *A61K 47/54* | (2017.01) |
| *A61K 9/00* | (2006.01) |

(52) U.S. Cl.
CPC .......... *A61K 9/5146* (2013.01); *A61K 9/0019* (2013.01); *A61K 9/513* (2013.01); *A61K 9/5161* (2013.01); *A61K 9/5192* (2013.01); *A61K 38/00* (2013.01); *A61K 47/549* (2017.08); *A61K 47/59* (2017.08); *A61K 47/6925* (2017.08); *C08G 73/02* (2013.01)

(58) Field of Classification Search
CPC .. A61K 9/5146; A61K 9/0019; A61K 47/549; A61K 47/59; A61K 47/6925; A61K 9/5161; A61K 38/00; A61K 9/5192; A61K 9/513; C08G 73/02
See application file for complete search history.

(56) References Cited

PUBLICATIONS

Chandrian et al, DNA Nanoparticles with Core-Shell Morphology, Soft Water; Author Manuscript, vol. 10, pp. 1-20 (Year: 2014).*

(Continued)

*Primary Examiner* — Carlos A Azpuru
(74) *Attorney, Agent, or Firm* — Sughrue Mion, PLLC

(57) ABSTRACT

Non-viral delivery platforms are provided for facilitating transport of molecules across cell membranes. In some forms, DNA nanoshells capable of transporting cargo molecules are formed, and may be formed in order to surround a variety of materials for a variety of purposes.

9 Claims, 1 Drawing Sheet

(56) References Cited

PUBLICATIONS

Li et al, Co-Delivery of Doxorubicin and Tumor-Suppressing p53 Using a POSS-Based Star-Shaped Polymer for Cancer Therapy, Biomaterials, vol. 55, pp. 1-12 (Year: 2015).*
Chandran. P. et al., DNA Nanoparticles With Core-Shell Morphology, Soft Matter; Author Manuscript, Oct. 14, 2014, vol. 10; 20 pp.
Li, Y. et al., Co-Delivery of Doxorubicin and Tumor-Suppressing p53 Gene Using a POSS-Based Star-Shaped Polymer for Cancer Therapy, Biomaterials, Apr. 9, 2015, vol. 55, 12 pp.
Patent Cooperation Treaty, International Search Report issued in International Application No. PCT/US2017/064245, dated Feb. 6, 2018, 2 pp.
Tenkumo, T. et al., Gene Transfection of Human Mesenchymal Stem Cells With a Nano-Hydroxyapatite-Collagen Scaffold Containing DNA-Functionalized Calcium Phosphate Nanoparticles, Genes to Cells, May 30, 2016, vol. 21, 16 pp.
Tian, Y. et al., Nuclease-Responsive DNA-PEI Hollow Microcapsules for Bio-Stimuli Controlled Release, Journal of Materials Chemistry B, Feb. 2014, vol. 2, 7 pp.

* cited by examiner

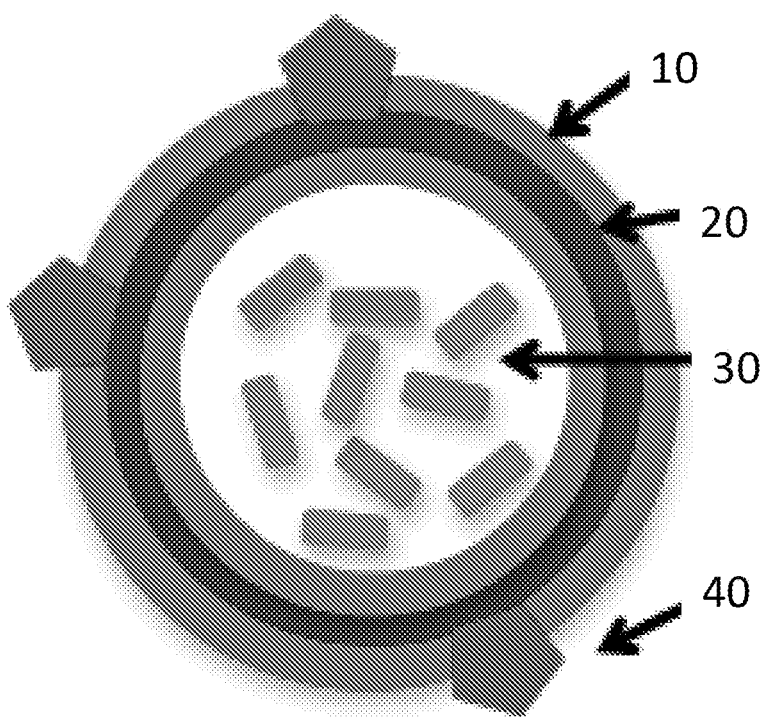

DEOXYRIBONUCLEIC ACID NANOPARTICLES FOR DELIVERING PROTEINS AND PROTEIN-CONTAINING COMPOUNDS AND METHODS OF MANUFACTURING DEOXYRIBONUCLEIC ACID NANOPARTICLES

CROSS-REFERENCE TO RELATED APPLICATIONS

This application is a U.S. national phase application filed under 35 U.S.C. § 371 of International Application PCT/US2017/064245, filed Dec. 1, 2017, designating the United States, which claims priority from U.S. Provisional Application No. 62/429,144, filed Dec. 2, 2016, both of which are incorporated herein by reference in their entirety.

BACKGROUND

It is often difficult for certain molecules to be transported across particular environments. For instance, many molecules have difficulty passing through cell membranes. The selective permeability of biological membranes to small molecules allows the cell to control and maintain its internal composition. Only small uncharged molecules can diffuse freely through such phospholipid bilayers; for instance small nonpolar molecules, such as $O_2$ and $CO_2$, are soluble in the lipid bilayer and therefore can readily cross cell membranes. Small uncharged polar molecules, such as $H_2O$, also can diffuse through membranes, but larger uncharged polar molecules cannot except through the action of transport proteins embedded in the membrane. Charged molecules, such as ions, are unable to diffuse through a phospholipid bilayer regardless of size; even H+ ions cannot cross a lipid bilayer by free diffusion, and must be transported across the membrane.

In some cases, transport across a cell membrane is facilitated by extracellular molecules or structures. For instance, certain chemicals will alter the permeability of a cell membrane's bipolar layer. As another example, viruses contain mechanisms to breach cell membranes, passing nucleic acids and/or proteins past the cell membrane and into the cell's cytoplasm. The receptors on viral envelopes, for instance, effectively become connected to complementary receptors on the cell membrane. This attachment causes the two membranes to remain in mutual proximity, favoring further interactions between surface proteins. In gene therapy and other applications, viral structures are often used as vectors to transport molecules across cell membranes and into cells. In order to replicate, viruses introduce their genetic material into host cells, tricking the host's cellular machinery into using it as blueprints for viral proteins. Retroviruses in particular induce copying of their genetic material into the genome of the host cell. Genetic engineers exploit viral mechanisms by substituting a virus's genetic material with therapeutic ribonucleic acids (RNA) or deoxyribonucleic acids (DNA). A number of viruses have been used for human gene therapy, including retroviruses, adenoviruses, herpes simplex, vaccinia, and adeno-associated virus.

Glycosylation is often used by viruses to shield underlying viral protein from immune recognition. Glycosylation is the reaction in which a carbohydrate, i.e. a glycosyl donor, is attached to a hydroxyl or other functional group of another molecule (a glycosyl acceptor). Glycosylation mainly refers in particular to the enzymatic process that attaches glycans to proteins, lipids, or other organic molecules. Glycans serve a variety of structural and functional roles in membrane and secreted proteins.

Non-viral vectors, transport molecules, and other methods for facilitating transport of other molecules across cell membranes present certain advantages over viral methods, such as capacity for large scale production and low host immunogenicity. However, existing non-viral methods also can produce lower levels of transfection and gene expression, and thus lower efficacy.

Methods for non-viral gene therapy include the injection of naked DNA, electroporation, gene guns, sonoporation, magnetofection, and the use of oligonucleotides, lipoplexes, dendrimers, and inorganic nanoparticles. There remains a need for improved non-viral transportation mechanisms.

SUMMARY

In one aspect of the invention, novel non-viral delivery platforms are provided for facilitating transport of molecules across cell membranes and into a cell nucleus. The delivery platforms may comprise deoxyribonucleic acid (DNA) nanoshells, which are small and dense but hollow particles of DNA, and may be formed in order to surround a variety of proteins and other materials for a variety of purposes. In some forms, the cargo carried by the nanoshells comprises proteins that bind DNA, such as nucleases, genetic markers, or other molecules active within the nucleus of cells. When DNA nanoshells encase proteins useful for gene therapy, DNA sequences and useful proteins are simultaneously delivered across the cell membrane and into the cell nucleus. This co-delivery of multiple gene therapy components improves efficiency and eliminates the need to provide separate vehicles for each type of molecule.

In some forms, nanoshells have a width or diameter of only a few nanometers, for instance from approximately 100 to 200 nm, and are formed by changing the spatial configuration of long DNA strands by introducing charged particles that induce changes in the shape of the DNA backbone. In some forms, the DNA nanoshells are approximately 150 nm in diameter. DNA has a semi-rigid backbone that occupies an expanded volume in solution, and is an anionic polymer by nature. When in the presence of polymeric cations (especially polymers having three positive charges or higher), the DNA backbone packs or condenses into less than one thousandth of its unperturbed volume. These condensed DNA particles may be used for delivering a variety of materials to cells in both clinical gene therapy and basic molecular biology applications. For instance, when the DNA is condensed around a protein molecule, the protein-containing particles more easily pass into cells than would the protein by itself due to inhibition of interactions between the proteins and cell membranes caused by the DNA shell that encases the protein.

In some forms, DNA nanoshells may be utilized to transport genetic sequences into cells simultaneously with enzymes or other proteins useful in transfection by forming a nanoshell from a DNA strand containing a sequence of interest for gene modification and packing the enzymes, proteins, or other useful molecules for gene therapy within the nanoshell. In this manner, multiple components for gene modification and/or modification of gene expression may be transported to the nucleus of a target cell at once without waste from unnecessary carrier molecules.

BRIEF DESCRIPTION OF FIGURES

FIG. 1 is a depiction of a cross-section of a nanoshell particle in accordance with some embodiments of the invention.

DETAILED DESCRIPTION

DNA may be combined with glycosylated polymer to form compact shells, for instance for the transport of molecules and other functions. In some embodiments, particles are formed comprising DNA collapsed around charged molecules, for example nucleases or restriction enzymes, polymerase, and/or other proteins active in the nucleus of cells. Amino acids and proteins, like other charged polar molecules, are not generally permeable to cell membranes. As a result, uptake of proteins is often very complex and highly specific. By encasing the protein molecules in a DNA nanoparticle comprising DNA and one or more cationic carriers, it is possible to take advantage of a cell's innate DNA transport mechanisms to deliver the packaged protein molecules from an extracellular source through the cell membrane and into the cytoplasm, and then into the nucleus.

In some forms, one or more nanoparticles are provided comprising deoxyribonucleic acid and at least one cationic glycosylated polymer, the nanoparticles each forming an interior space, the nanoparticles having a diameter of from about 50 nm to about 250 nm, with at least one protein disposed within the interior space. The glycosylated polymer may comprise, a charged polymer and a small mono or disaccharide, for instance, polyethylenimine in combination with mannobiose. The protein disposed within the nanoparticle may be a DNA binding protein. In some forms, the nanoparticle comprises a glycan shell on an exterior surface and/or interior surface thereof. The interior surface may in some embodiments form a generally spherical interior space with the nanoparticle substantially covered on an interior surface of the nanoshell by a glycan shield.

In some forms, a method for co-localization of DNA and protein is provided that comprises combining DNA and charged glycosylated polymer in a solution having less than 100 mM salt concentration to form a nanoshell precursor; combining the nanoshell precursor with a DNA binding protein to form a protein-packed nanoshell; and introducing the protein-packed nanoshell into a cell.

In some forms, a method for protecting toxic or enzymatic proteins from an environment is provided that comprises combining a nucleic acid and a glycosylated polymer in solution separated from the environment to form a nanoshell precursor, adding the toxic or enzymatic protein to the solution before the nanoshell precursor has fully formed into a nanoshell, and thereafter introducing the fully formed nanoshell into the environment.

In some embodiments, solutions of double stranded deoxyribonucleic acid (dsDNA) and polyethylenimine (PEI) with mannobiose bristles are formulated to produce self-assembling nanoshells of DNA around relevant proteins. PEI is a positively charged polyelectrolyte and binds to negatively charged DNA. The resulting charge-neutralized hydrophobic complex self-packs in a sequential pathway to produce condensed nanostructures. Different solution conditions elicit different pathways to produce nanostructures ranging from two-dimensional rods and toroids (doughnut-shaped) to three-dimensional globules and disordered nano-aggregates. Atomic force microscope (AFM) image and scanning electron microscope (SEM) imaging confirms a homogenous distribution of molecules representative of globules or aggregates results when a complex of DNA and PEI alone, but a different result is achieved when DNA is combined with PEI having mannobiose bristles (PEIm). The carbohydrate interactions of the mannose bristles of the PEI backbone may be manipulated to divert the DNA condensation pathway into producing hollow, three-dimensional shells, and imaging indicates a circumferential distribution of DNA indicative of a nanoshell structure. During the condensation pathway for shell packing, a phase-separation of the mannobiose bristles occurs on the inner and outer surfaces of a DNA-PEIm rich shell.

In some embodiments, the condensation pathway of a complex of DNA and carbohydrate-modified cationic polymer (such as Mannobiose-modified polyethylenimines) can be manipulated to pack and stabilize proteins on the inside while also forming a self-sealing glycan shield studded with cell-specific ligands on the outside. Low salt concentrations, such as from 0 to 100 mM salt, induce packing of the DNA-glycosylated PEI in a manner that forms a dense glycan shield. In other words, the combination of DNA, polymer, and sugars may be used to produce an 'inverted virus' platform which combines the advantages of viral- and polymer-based co-delivery. However, unlike natural virus particles, the nanoshells have a glycan shield on both the inside and outside of the shell structure, and the shell itself comprises DNA rather than the oligomers and lipids of a virus capsid. As shown in FIG. 1, one such virus-like nanoshell platform constructed from DNA and mannobiosylated PEI includes a mannobiose shield (10) on both sides of a condensed DNA-PEI shell (20) with cell-specific ligands (40) extending therefrom. Cargo (30) such as proteins may be enveloped within the DNA-PEI shell. The glycan shield of such particles provides a synthetic means to mimic beneficial properties of biological virus particles, such a protective glycan shields, reduced non-specific membrane interactions, internal packaging of molecules, and protection of nucleic acids. According to Atomic Force Spectroscopy, the mannobiose bristles of the nanoshells exhibit self-adhesion and packing interactions similar to the glycan shield of a virus-like particle.

The nanoparticles may be prepared by combining DNA and one or more cationic polymers in solution. Optionally, one or more saccharides may be reacted with the cationic polymer before combination with DNA. Preferably, the ratio of DNA to cationic polymer is less than 1 bp:0.1 amine, more preferably 1 bp:3 amine, and even more preferably 0.1 bp:1 amine. The solution may be incubated for 10 min to 24 hours in order to allow the DNA to condense and the nanoparticles to form, and thereafter the nanoparticles may be removed or concentrated by any known method, such as centrifugation. Low salt concentrations are responsible for formation of a glycan shield on the outside and inside surfaces of the nanoparticle. The condensation solution may be, for instance, water containing 0 to 100 mM sodium chloride Optionally, additional compositions may be combined with DNA and cationic polymer in solution in order to incorporate those compositions into nanoparticles during formation. It has been discovered, however, that incorporating proteins or other charged particles can disrupt formation of DNA nanoparticles by competitively inhibiting interactions between the cationic polymer and DNA molecules. Surprisingly, a technique has been developed to avoid disruption of nanoparticle formation by delaying addition of proteins until about 5 seconds to about 25 minutes, preferably about 1 to about 10 minutes, after combining DNA and cationic polymer, thus giving the DNA nanoparticles a short time to begin formation. After the delay, proteins are added to the solution, and the DNA particles continue to form around encountered proteins without significant disruption, forming a nanoparticle comprising protein encased within a tightly packed DNA shell. Centrifugation, filtration, and/or drying may be used to remove excess polymer, protein, and DNA, resulting in retrieval of a purified composition comprising protein-containing DNA nanoshells.

In some forms, DNA for use in the invention may be from any number of sources and of any length, although preferably 1 kB to 20 kB. In one form, the DNA may be plasmid DNA comprising approximately 12.5 kilobases.

In some forms, polymers for use in the current invention generally have a mass of about 10 to about 100 kDa, preferably 18 to 30 kDa, and are hydrophobic and charged. The polymers may be glycosulated, and in some forms contain mannobiose or other carbohydrate bristles along a portion or substantially the entire length of the polymer. Polyethyleneimine (PEI) is one preferred cationic DNA carrier for use in constructing DNA nanoparticles, due in part to its close arrangement of positively charged amine groups on its backbone that make the polymer effective at neutralizing DNA and condensing it into stable nanoparticles. Only about half of the PEI amines are protonated and charged at physiological pH. Additional protonation occurs at lower pH and the polymer functions like a buffer. The 'proton-sponge' character of PEI is also useful for stabilizing DNA nanoparticles in the acidic environment of cell uptake vesicles, and for subsequent osmotic bursting of these vesicles to release the nanoparticles into the cytoplasm. Studies have indicated that PEI-DNA nanoparticles may be actively transported to the vicinity of the cell nucleus. The linking of compounds to the PEI backbone of DNA-PEI nanoparticles can improve the morphological, cytotoxicity, and cell targeting characteristics of the DNA-PEI complex.

Mannobiose-modified polyethylenimines and similar molecules also may be used to generate nanoparticles of DNA that can be targeted to the antigen-presenting cells of the immune system to deliver amino acids and proteins to selected cells or areas of the body. Saccharides such as Mannobiose, polyethylene glycol, trehalose, fucose, and galactose may be grafted to the backbone of the cationic DNA carrier in order to generate DNA particles that can be targeted to the Antigen-Presenting Cells (APCs) of the immune system. Nanoshells comprising DNA can be useful in immunotherapies that load antigen-presenting cells (APCs) with antigens against cancer and AIDS, to ensure a sustained and long-term immune response against these conditions.

RNA and proteins are extremely labile macromolecules that need to be sequestered into capsules for delivery (e.g. within the shell of a virus). The core of the DNA shell can similarly serve to sequester cargo that is labile to the trafficking pathway (e.g. the acidic environment of endosomes) or is foreign to the host cell and elicits an immune response. In addition, the layer of mannobiose inside the shell can function to entrap and stabilize proteins, since sugars like mannose have been shown to preferentially hydrate and stabilize protein conformation.

In some forms, DNA-PEI nanoshells also may facilitate trafficking of cargo to the nucleus of cells. Foreign matter entering the cell can become trapped in endosomes, can break down in lysosomes, or can remain 'stuck' in the low-diffusive 'crowded' cytoplasm. Viruses have evolved means to overcome these barriers and deliver their DNA to the cell nucleus. While PEI has been shown to localize towards the nucleus, the PEI polymer alone is a weak base and buffers the DNA in the endosome, which leads to its osmotic rupture. In the cytoplasm, PEI-based carriers actively transport to the nucleus via the microtubular system. The DNA nanoshells comprising PEI retain the nuclear trafficking property of PEI, so there is no need to tag a Nuclear Localization Signal to any of its components to enable access to genomic DNA in the nucleus.

In some forms, the nanoshells may also reduce extraneous carrier material in comparison to other carrier molecules and structures. For instance, in a generic virus, DNA or RNA is carried inside a protein shell (or capsid) that can potentially be lipid-coated. The main purpose of the shell is packaging and protection of the viral genomic nucleic acid. In the DNA nanoshells, in contrast, the principal packaging component is the DNA being delivered, so that the carrier itself is a useful component and is capable of entering a cell nucleus along with its cargo. Unlike other non-viral delivery techniques, extraneous material does not provide all of the packaging (e.g., lipids in liposomes, polymers in polymer-based carriers, hard and metallic nanoparticles in magnetofection, etc.). By engineering the DNA to be part of the packaging material, the amount of carrier polymer needed for transfection is minimized, thereby reducing the potential toxicity from excess foreign polymer when they are shed inside of cells and tissues.

In some forms, DNA-polymer nanoshells may be utilized for directly transfecting proteins to permit high-throughput screening of proteomics data for phenotype-mapping, decoding biological mechanisms, and testing therapies. DNA and proteins can be simultaneously transported when a DNA sequence of interest is compacted to form a shell around proteins of interest. Through direct protein transfection, the time-consuming step of generating transfection plasmids can be bypassed and the functional effect of the transfected proteins is seen immediately (e.g. 1-2 hours compared to 18-48 hours for DNA transfection). These methods avoid reliance on potentially incompatible host post-translational machinery (e.g. mammalian cells producing bacterial proteins), and studies can also be performed in slow- or non-dividing cells (e.g. macrophages, cardiac/retinal/neuronal cells) which do not effectively produce proteins from transfected DNA.

I claim:

1. A nanoparticle comprising deoxyribonucleic acid and at least one cationic glycosylated polymer, the nanoparticle forming an interior space, the nanoparticle having a diameter of from about 50 nm to about 250 nm, and at least one protein disposed within the interior space.

2. The nanoparticle of claim 1, wherein the glycosylated polymer comprises polyethylenimine.

3. The nanoparticles of claim 1, wherein the glycoslylated polymer comprises mannobiose.

4. The nanoparticle of claim 1, wherein the at least one protein is a DNA binding protein.

5. The nanoparticle of claim 1, further comprising at least one genetic marker disposed substantially within a cavity of the nanoparticle.

6. The nanoparticle of claim 1, the nanoparticle comprising a glycan shell on at least an exterior surface thereof.

7. The nanoparticle of claim 6, further comprising a glycan shell on an interior surface of the nanoparticle.

8. The nanoparticle of claim 7, wherein the interior surface forms a generally spherical interior space within the nanoparticle substantially covered on an interior surface of the nanoshell by a glycan shield.

9. The nanoparticle of claim 7, wherein the interior surface forms a generally spherical interior space within the nanoparticle, and the nanoparticle further comprises at least one protein disposed within the interior space.

* * * * *